United States Patent [19]

Reukauf

[11] 3,999,562
[45] Dec. 28, 1976

[54] TOOTHPICK CONSTRUCTION
[76] Inventor: William B. Reukauf, 31 Colonial Ridge Drive, Haddonfield, N.J. 08033
[22] Filed: Feb. 24, 1976
[21] Appl. No.: 660,803
[52] U.S. Cl. ............................................. 132/89
[51] Int. Cl.² ....................................... A61C 15/00
[58] Field of Search ........................ 132/89, 90, 61
[56] References Cited
UNITED STATES PATENTS 3,491,776  1/1970  Fleming ......................... 132/89
3,511,249  5/1970  Baitz ............................ 132/89

Primary Examiner—G.E. McNeill
Attorney, Agent, or Firm—Robert K. Youtie

[57] ABSTRACT

A toothpick including an elongate body having ribs in longitudinally extending angularly spaced relation, the ribs being resiliently deflectable to change the angular spacing for entry into and cleaning manipulation within intertooth spaces.

8 Claims, 9 Drawing Figures

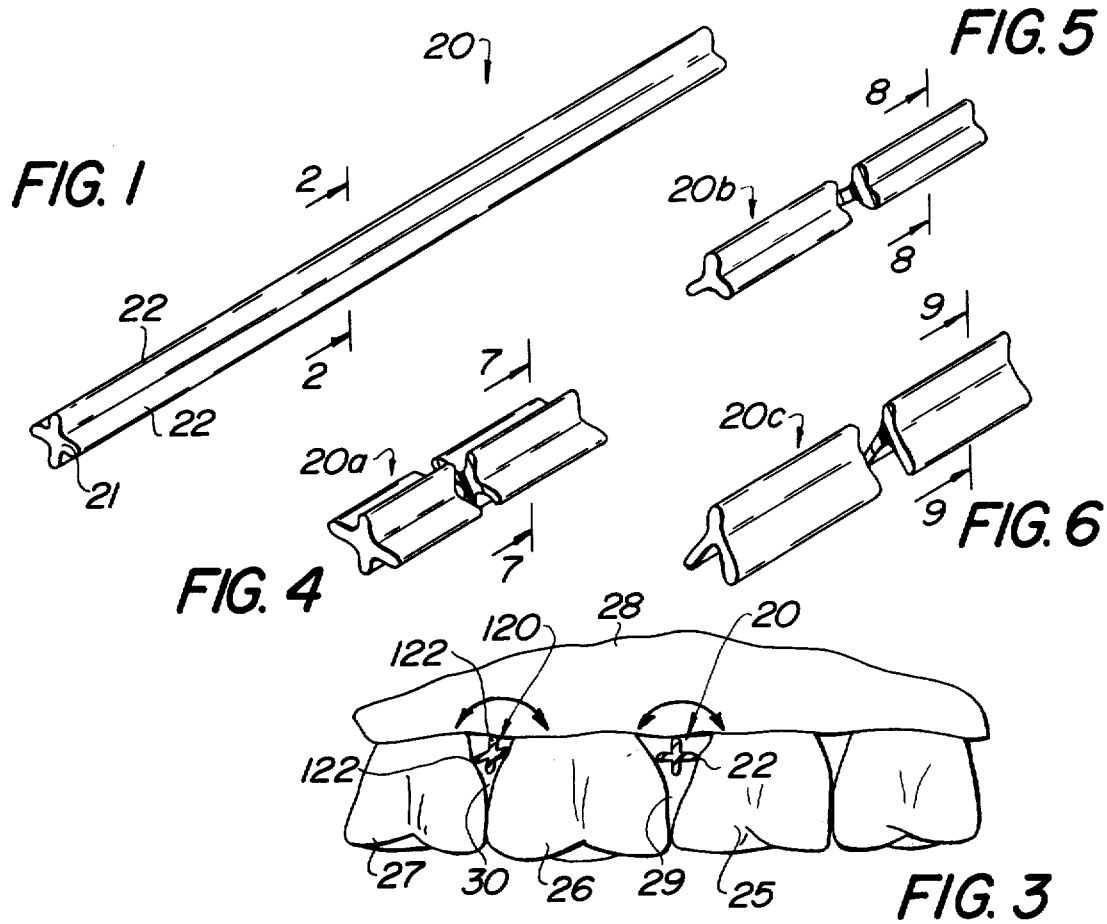

3,999,562

TOOTHPICK CONSTRUCTION

BACKGROUND OF THE INVENTION

As is well known, conventional toothpicks are generally fabricated of wood, and usually assume the double-ended, round section configuration, or the tapered flat section configuration. The round cross-section type is relatively thick and cannot pass very far through the intertooth spaces, while the flat section type is relatively weak and easily broken in use. There are also the quill type, both natural and artificial, which are extremely expensive, and plastic imitations of the wooden types which are expensive and subject to the same drawbacks as wood.

SUMMARY OF THE INVENTION

Accordingly, it is an important object of the present invention to provide a highly improved toothpick construction which overcomes the above-mentioned prior art difficulties, being capable of relatively thinned proportioning for ease of entry into and considerable insertion through intertooth spaces, facilitating rotary as well as longitudinal movement to effectively wipe or scrape away undesired material even in relatively small intertooth spaces, while beneficially massaging the gums without injury thereto.

It is another object of the present invention to provide a toothpick construction having the advantageous characteristics mentioned in the preceding paragraph which is flexible but effectively resists breakage in use, and of a conformably deflectable cross-section for entry into variously shaped and size intertooth spaces, while being longitudinally bendable by the user, without breakage, to enhance access to and operation upon posterior teeth.

It is still another object of the present invention to provide a toothpick construction of the type described which is safe, durable and reliable, while capable of economic mass production for distribution and sale at a reasonable price.

Other objects of the present invention will become apparent upon reading the following specification and referring to the accompanying drawings, which for a material part of this disclosure.

The invention accordingly consists in the features of construction, combinations of elements, and arrangements of parts, which will be exemplified in the construction hereinafter described, and of which the scope will be indicated by the appended claims.

BRIEF DESCRIPTION OF THE DRAWINGS

FIG. 1 is a perspective view showing a toothpick constructed in accordance with the teachings of the present invention.

FIG. 2 is a transverse sectional view, enlarged for clarity, taken generally along the line 2—2 of FIG. 1.

FIG. 3 is a partial front view showing a user's teeth and illustrating, in cross-section, toothpicks of the present invention in operative conjunction with the teeth and gums.

FIGS. 4, 5 and 6 are each a perspective, broken away view showing a respective modification of toothpick constructed in accordance with the teachings of the present invention.

FIGS. 7, 8 and 9 are respective cross-sectional views taken on FIGS. 4, 5 and 6, enlarged for clarity.

DESCRIPTION OF THE PREFERRED EMBODIMENTS

Referring now more particularly to the drawings, and specifically to FIGS. 1–3 thereof, a toothpick is there generally designated 20, and may advantageously be integrally fabricated of suitably flexible, resilient plastic, say vinyl or other, as desired.

More particularly, the toothpick construction 20 includes a longitudinally extending central part or body 21, and a plurality of radially outstanding, longitudinally extending ribs 22 on the central part 21.

While the toothpick 20 composed of the central part 21 and radially extending ribs 22, is flexible along its longitudinal axis, as a unit, it is normally straight, as illustrated, in its undeflected or rest condition. Further, as in the illustrated embodiment of FIG. 1, the ribs 22 are longitudinally coextensive with the central part 21, and combine to define a constant cross-sectional configuration throughout the entire length of the toothpick construction 20. This facilitates economy of manufacture, as by extrusion and severance to desired length. However, the toothpick of the present invention may be otherwised manufactured, as by injection molding, and is not necessarily of constant cross-section throughout its length.

Referring further to the illustrated embodiment of FIGS. 1 and 2, it will there be apparent that there are illustrated four ribs 22, all radiating from the central part 21 and in equiangularly spaced relation about the latter. Therefore, the four ribs 22 are spaced 90° from adjacent ribs, as best seen in FIG. 2. Further, the ribs 22 are each of a thickness or dimension normal to the radial extent approximately equal to the transverse dimension of the central part; and, the distal or outer edge surface 23 of each rib is preferably smoothly convexly curved, for a purpose appearing presently. However, the ribs may be thinner, if desired.

In the illustrated embodiment of FIGS. 1 and 2, the maximum overall transverse dimension, as between opposite rib edge surfaces 23, has been found to advantageously approximate 0.025 inches. This transverse dimension has been found sufficiently small to permit of easy entry into even relatively small intertooth spaces, and has been found large enough so that manipulation of the toothpick by axial rotation effectively wipes, scrapes or otherwise dislodges undesired material, while beneficially massaging the user's gums, without injury thereto. Such rotative action may be conveniently achieved by merely rotating the toothpick 20 between the user's thumb and forefinger.

This operative use in a person's mouth may be seen in FIG. 3, wherein are shown a plurality of adjacent teeth 25, 26 and 27 depending from the gum 28. Extending through the space 29 between teeth 25 and 26 is a toothpick construction 20. It will there be seen that the toothpick 20 may be inserted into and axially rotated within the space 29 without appreciable resilient deflection of the ribs 22. However, a smaller intertooth space is shown at 30, between adjacent teeth 26 and 27, wherein is inserted a substantially identical toothpick 120. However, it will there appear that the toothpick 120 has its several ribs 122 resiliently distorted or deflected, say to alter the interrib angular spacing, to accommodate the cross-sectional configuration of toothpick 120 for entry into the intertooth space 30. Here also, it will be appreciated that the toothpick 120 may be rotated within the space 30, but such rotation will effect resilient deflection of the ribs 122, while the latter accomplish the hereinbefore described cleaning and massaging function. Such rotation is shown by arrows in FIG. 3.

It will also be appreciated that the toothpick 120, by its resilient flexibility or deflectability about the longitudinal axis will greatly simplify the cleaning and massaging operation upon the harder-to-reach rear or posterior teeth. If desired, the toothpick 20 may be considerably longer than a conventional toothpick to permit bending in the user's mouth, as required, for engagement with rear teeth.

While the toothpick 20 of FIGS. 1 and 2 is illustrated and described as having ribs 22 of equal radial extent, it is appreciated that the ribs are not necessarily of equal radial extent, but may be of different radial extent, as in FIGS. 4 and 7, so as to describe other than a circular cross-sectional configuration, say an ovaloid cross-sectional configuration.

More particularly, a toothpick 20a shown in FIGS. 4 and 7 includes a longitudinal central part 21a and a plurality, namely four equiangularly spaced ribs, one opposed pair being designated 22a, and the other opposed pair being designated 122a. As in the first described embodiment, the toothpick 20a may be integrally fabricated of plastic, or other suitable material, being of substantially constant cross-section throughout its length. However, while the ribs 22a and 122a are equiangularly spaced about the central part 21a, the ribs may be of different radial extent. As illustrated, one opposed pair of ribs 22a may be of equal radial extent and relatively short, while the other opposed pair of ribs 122a may be of equal radial extent and greater than that of the ribs 22a. Further, it is not necessary that opposed ribs be of equal radial extent, but may also be of different radial extent.

By such variation in cross-sectional configuration, different cleaning and massaging characteristics may be achieved, as desired.

Further additional operating characteristics may be achieved by varying the number of ribs, as in the embodiment of FIGS. 5 and 8, wherein is illustrated a toothpick construction 20b having a plurality of ribs less than four in number, namely being three equally angularly spaced apart ribs 22b extending radially from a longitudinal center part 21b.

As in the first two described embodiments, the toothpick 20b may be integrally fabricated of resiliently flexible plastic, say of constant cross-sectional configuration, and afford a variation in the characteristics of entry, cleaning and massaging which may be preferred in certain circumstances. For example, the radial extent of the several ribs 22b may be substantially equal, so that each generates an identical cylindrical surface of generation upon rotational manipulation, while the reduced number of ribs 22b insures self-maintenance in the at-rest straight condition, while permitting of easier flexibility for entry between the spaces of more remote teeth.

A further slight variation is shown in FIGS. 6 and 9, wherein a toothpick 20c is generally similar to toothpick 20b, including a longitudinal center part 21c, and three equiangularly spaced longitudinally extending, radially projecting ribs, one being designated 22c and the remaining two each being designated 122c. In this embodiment, the radial extent of the several ribs 22c and 122c is not equal, one being different than the other two. In particular, the radial extent of rib 22c is illustrated as less than that of each rib 122c. If desired, the radial extents of respective ribs 122c may also be different.

Hence, additional different characteristics in operation may be achieved by the embodiment of FIGS. 6 and 9, the cross-sectional configuration describing other than a circle.

From the foregoing, it is seen that the present invention provides a toothpick construction which is extremely simple in structure, lends itself to economic methods of manufacture, is adapted for greater ease in use, and otherwise fully accomplishes its intended objects.

Although the present invention has been described in some detail by way of illustration and example for purposes of clarity of understanding, it is understood that certain changes and modifications may be made within the spirit of the invention.

What is claimed is:

1. A toothpick construction comprising an elongate central part, and a plurality of longitudinal ribs extending along said central part in angulately spaced relation thereabout, said ribs being resiliently deflectable to change said angulately spaced relation for entry into and cleaning manipulation within intertooth spaces.

2. A toothpick construction according to claim 1, said central part and ribs being integral and of substantially constant cross-section throughout the longitudinal dimension.

3. A toothpick construction according to claim 2, said central part and ribs being of plastic material.

4. A toothpick construction according to claim 1, said ribs being at least three in number.

5. A toothpick construction according to claim 4, said angularly spaced relation of ribs being equiangular.

6. A toothpick construction according to claim 5, said ribs all being of substantially equal radial extent, to facilitate rotation in said intertooth spaces.

7. A toothpick construction according to claim 5, said ribs being of unequal radial extent for enhanced cleaning action upon rotative movement in said intertooth spaces.

8. A toothpick construction according to claim 1, said central part and ribs being resiliently flexible, to enable obtaining an arcuate configuration within a user's mouth.

* * * * *